United States Patent [19]

DeClippeleir et al.

[11] Patent Number: 4,772,456

[45] Date of Patent: Sep. 20, 1988

[54] PROCESS FOR PREPARING CRYSTALLINE SILICAS

[75] Inventors: Georges E. M. J. DeClippeleir, Sint-Pieters-Leeuw; Raymond M. Cahen, Brussels; Hugo Van Thillo, Grimbergen; Guy L. G. Debras, Belgrade, all of Belgium

[73] Assignee: Labofina, S.A., Brussels, Belgium

[21] Appl. No.: 562,652

[22] Filed: Dec. 19, 1983

[51] Int. Cl.[4] .............................................. C01B 33/20
[52] U.S. Cl. ...................................... 423/328; 423/326; 502/77
[58] Field of Search .................................. 423/328–332, 423/335; 502/60, 77, 232

[56] References Cited

U.S. PATENT DOCUMENTS 3,702,886  11/1972  Argauer et al. ..................... 423/328
4,061,724  12/1977  Grose et al. ......................... 423/335

OTHER PUBLICATIONS

Wu et al., "Journal of Physical Chemistry", vol. 83, No. 21, 1979, pp. 2777–2781.

*Primary Examiner*—John Doll
*Assistant Examiner*—R. Bruce Breneman
*Attorney, Agent, or Firm*—William D. Jackson; John K. Abokhair; M. Norwood Cheairs

[57] ABSTRACT

Disclosed is a process for preparing crystalline silicas having the monoclinic symmetry which comprises the step of calcining in air for at least 3 hours at a temperature of at least 500° C. a crystalline silica of the silicalite type having a silica to alumina atomic ratio of at least 80.

15 Claims, No Drawings

PROCESS FOR PREPARING CRYSTALLINE SILICAS

TECHNICAL FIELD

The present invention relates to a process for preparing crystalline silicas, more particularly, crystalline silicas having a structure with monoclinic symmetry.

The crystalline silicas prepared in accordance with the process of the present invention exhibit molecular sieve properties and catalytic properties in the field of reactions requiring shape selectivity, as for instance alkylation and isomerization.

BACKGROUND ART

During the last ten years, many efforts have been made to find new types of catalysts, either in the zeolitic field, or in the crystalline silica field.

One problem with zeolitic type catalysts is that they are subject to rapid deactivation in the presence of even small amounts of water. Rapid deactivation means that a high rate of conversion of reactants to products cannot be maintained over a long period of time thus requiring expensive catalyst changeouts or regeneration procedures which greatly reduce the efficiency of the overall process.

More recently, crystalline silicas of the silicalite type, as prepared in U.S. Pat. No. 4,061,724, have been recognized to be of the orthorhombic symmetry and to have steam stability.

It has also been recently reported that silicalite type crystalline silicas exhibit some shape selectivity in the presence of steam. Greater shape selectivity than is obtainable with such previously existing materials would be desirable.

The Applicants have disclosed in a co-pending application that crystalline silicas of monoclinic symmetry have interesting shape selective properties.

There is, therefore, a need for a process to prepare a crystalline silica catalyst having the monoclinic symmetry.

SUMMARY OF THE INVENTION

It is therefore an object of the present invention to provide a new process for specifically preparing a crystalline silica catalyst having the monoclinic symmetry.

Another object of the present invention is to provide a process for preparing a crystalline silica catalyst having the monoclinic symmetry, said catalyst having excellent catalytic activity in reactions requiring shape selectivity and particularly in para alkylation reactions.

Another object of the present invention is to provide a process for preparing a crystalline silica catalyst having the monoclinic symmetry, said catalyst having not only excellent catalytic activity, but exhibiting excellent steam stability.

The process according to the present invention for preparing crystalline silicas having the monoclinic symmetry comprises the step of calcining in air for at least 3 hours at a temperature of at least 500° C. a crystalline silica of the silicalite type having a silica to alumina atomic ratio not lower than about 80.

DETAILED DESCRIPTION OF THE INVENTION

The term crystalline silicas having the monoclinic symmetry when used in the present invention means a crystalline silica having, after calcination, in accordance with the process of the invention, a specific X-ray diffraction pattern. Such an X-ray diffraction pattern is given in Table 1.

TABLE 1

| Interplanar spacing of d (Angstroms) | Relative intensity |
|---|---|
| 11.33 | 100 |
| 10.18 | 52 |
| 9.89 | 22 |
| 6.76 | 10 |
| 6.41 | 16 |
| 6.05 | 20 |
| 5.74 | 11 |
| 5.61 | 14 |
| 5.17 | 3 |
| 5.06 | 7 |
| 5.01 | 8 |
| 4.64 | 7 |
| 4.38 | 9 |
| 4.28 | 11 |
| 4.10 | 5 |
| 4.03 | 7 |
| 3.87 | 82 |
| 3.83 | 42 |
| 3.77 | 22 |
| 3.73 | 48 |
| 3.67 | 15 |
| 3.64 | 15 |
| 3.61 | 4 |
| 3.50 | 5 |
| 3.46 | 7 |
| 3.41 | 4 |
| 3.37 | 7 |
| 3.33 | 7 |
| 3.32 | 11 |
| 3.27 | 5 |
| 3.15 | 3 |
| 3.06 | 6 |
| 3.05 | 6 |
| 3.00 | 15 |
| 2.95 | 7 |
| 2.74 | 4 |
| 2.69 | 3 |
| 2.60 | 3 |
| 2.52 | 4 |
| 2.49 | 5 |
| 2.42 | 4 |
| 2.02 | 10 |
| 2.00 | 9 |
| 1.88 | 3 |

One of the most important features of the X-ray diffraction pattern of the crystalline silicas of the invention is constituted by the splitting of the peak at the interplanar spacing of about $d = 3.65 \pm 0.02$ Å.

Other features of the X-ray diffraction pattern which may be used to distinguish the crystalline silicas having the monoclinic symmetry from others, may be exemplified by the appearance of a doublet at the interplanar spacing of about $d = 3.05$ to $3.06$ Å, while a singlet peak appears at the interplanar spacing of about $d = 3.00 \pm 0.02$ Å.

The crystalline silica of the silicalite type which has to be used to manufacture the catalyst of the monoclinic symmetry of the invention may be prepared by hydrothermal crystallization of a reaction mixture containing water, a source of silica, an alkali metal oxide and a quaternary ammonium salt having the formula (I)

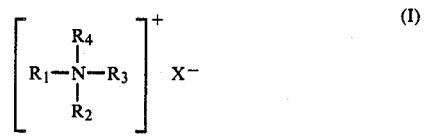

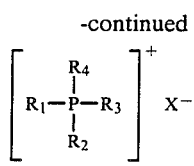

or a quaternary phosphonium salt having the formula (II), wherein $R_1$, $R_2$, $R_3$ and $R_4$ are alkyl radicals, and X is OH or radical of a monovalent acid, at a pH between 7 and 14, to form a hydrous crystalline precursor.

The source of silica in the reaction mixture is generally selected from alkali metal silicate, fume silica, silica sols and silica gel.

It has been noticed that these silica sources always contain minor amounts of alumina.

According to the present invention, the amount of alumina which may be present in the crystalline silica should be such that the silica-alumina atomic ratio is not lower than 80. Preferably, silica-alumina atomic ratios should be higher than 120 while ratios higher than 200 or even 2000 may also be found.

In case of the very high silica to alumina atomic ratios, the silica source to be used may be obtained by preparing a gel by controlled hydrolysis of tetraethylsilicate.

The other compound which is to be considered in the preparation of the crystalline silica is the quaternary ammonium salt, which is generally selected from the group comprising tetrapropylammonium bromide or hydroxide and tetraethylammonium bromide or hydroxide, the tetrapropylammonium bromide being preferred.

Accordingly, in preparing the crystalline silicas, there is formed a reaction mixture, having a pH of at least 10, which contains from 150 to 700 moles $H_2O$, 13 to 50 moles silica and from 0.1 to 6.5 moles $M_2O$ wherein M is an alkali metal, per mole-ion of the quaternary cation. The reaction mixture is maintained at a temperature from about 100 to 250° C. under autogeneous pressure until crystals of the silica are formed, ordinarily after about 50 to 150 hours. The obtained product, which is a crystalline silica of the silicalite type, is washed with water and dried in air at about 110° C.

The process for specifically preparing the crystalline silica catalyst of the monoclinic symmetry comprises the step of calcining the hereabove prepared product, in air for a period of time of at least 3 hours at a temperature of at least about 500° C.

The Applicants have found that a calcination of crystalline silicas of the silicalite type during a period of time of less than about 3 hours does not lead to suitable catalysts even at temperatures exceeding about 850° C. On the other hand, crystalline silicas of the silicalite type but having silica to alumina atomic ratio less than about 60 which are calcined at a temperature comprised between 550 and 650° C. during a period of time as long as 168 hours do not exhibit a monoclinic symmetry.

According to an embodiment of the process of the present invention, the calcination time of the crystalline silicas of the silicalite type is generally comprised between 3 and 96 hours, preferably between 5 and 72 hours, provided that the silica to alumina atomic ratio is higher than 80.

The calcination temperature is also an important factor. The temperature should be sufficient to obtain a monoclinic symmetry but should not be too high and, in any case, should not exceed 800° C. in order to avoid the transformation of the crystalline silica into other forms such as cristobalite.

Generally the calcination temperature is comprised between 550 and 650° C.

The following examples are given in order to better illustrate the process of the present invention, but without limiting its scope.

EXAMPLE 1

A crystalline silica catalyst was prepared by mixing 103 grams of colloidal silica containing 0.8% $Na_2O$ in 250 grams water with 24.3 grams of $(C_3H_7)_4N^+Br^-$ in 62 grams $H_2O$; 9.1 grams NaOH in 62 grams $H_2O$ were added to the mixture. During the synthesis the pH of the mixture has varied from 12.7 to 11.7. Afterwards the mixture was heated at 175° C. in an autoclave for 3 days. The resulting crystalline silica of the silicalite type has the following molecular formula expressed in terms of oxide:

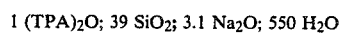

1 (TPA)$_2$O; 39 SiO$_2$; 3.1 Na$_2$O; 550 H$_2$O

The present crystalline silica of the silicalite type had a silica/alumina atomic ratio of 450.

This crystalline silica was then calcined in the presence of air for 10 hours at 600° C. The calcined crystalline silica had an X-ray diffraction pattern which presents a doublet at the interplanar spacing d = 3.65 Å. In addition, the X-ray pattern presents a doublet at about d = 3.05 to 3.06 Å and a singlet at about 2.98 to 3.00 Å. Said crystalline silica belonged to the monoclinic symmetry class.

COMPARISON 1A

By way of comparison, the same crystalline silica of the silicalite type as hereabove described, was calcined for 1 hour at 475° C. The calcined crystalline silica does not have any of the features which may characterize the monoclinic symmetry.

EXAMPLE 2

The crystalline silica having the monoclinic symmetry prepared in Example 1 was used to carry out the alkylation of toluene by ethylene in the presence of steam at the following operating conditions:

Toluene/ethylene mole ratio: 8.1
Water/toluene mole ratio: 0.2
Inlet temperature: 410° C.
Pressure: 15 kg/cm$^2$
Toluene WHSV: 187.5

At a 55% ethylene conversion, ethyltoluene has been obatained with a para/meta isomer ratio of 7.4.

By way of comparison, the crystalline silica of the silicalite type prepared in the Example Comparison 1A, has been tested in the same conditions as hereabove described.

At a 55% ethylene conversion, ethyltoluene has been obtained with a para/meta isomer ratio of 2.7.

This example shows the advantage of the process of the invention to prepare suitable catalyst for alkylation reaction of alkylaromatic hydrocarbons.

EXAMPLE 3

A crystalline silica catalyst was prepared by mixing 370.4 grams of colloidal silica containing 0.12% $NA_2O$ in 250 grams water with 38 grams of $(C_3H_7)_4N^+Br^-$ in 200 grams $H_2O$; 15.7 grams NaOH in 200 grams $H_2O$ were added to the mixture. During the synthesis the pH of the mixture has varied from 13.1 to 12. Afterwards the mixture was heated at 175° C. in an autoclave for 3 days. The resulting crystalline silica of the silicalite type has the following molecular formula expressed in terms of oxide:

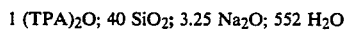

The present crystalline silica of the silicalite type has a silica to alumina atomic ratio of 130. This crystalline silicalite has been calcined in the presence of air for 3 hours at 600° C. The calcined crystalline silicalite had an X-ray diffraction pattern which presents a doublet at the interplanar spacing d=3.65 Å. Said crystalline silica belonged to the monoclinic symmetry class.

This crystalline silica was used in an alkylation reaction as described in Example 1.

At 70% ethylene conversion, ethyltoluene has been obtained with a para/meta isomer ratio of 4.8.

COMPARISON 2A

By way of comparison, the same crystalline silica of the silicalite type as hereabove prepared was calcined for 1 hour at 500° C.

The calcined crystalline silica does not have any of the features which may characterize the monoclinic symmetry.

This crystalline silica was tested in an alkylation reaction, the operating conditions of which have been described hereabove.

At 70% ethylene conversion, ethyltoluene has been obtained with a para/meta isomer ratio of 2.4.

COMPARISON 2B

An aluminosilicate having a silica to alumina atomic ratio of 40 has been calcined for 72 hours at a temperature of 600° C.

At this time the aluminosilicate does not have any of the features which may characterize the monoclinic symmetry.

The calcination has been repeated for 168 hours at 600° C. without bringing any change in the symmetry.

We claim:

1. A process for preparing crystalline silicas having the monoclinic symmetry which comprises the step of calcining in air for at least 3 hours at a temperature of at least 500° C. a crystalline silica of the silicalite type having a silica to alumina atomic ratio of at least about 80.

2. A process according to claim 1 wherein the crystalline silica of the silicalite type is calcined in air for a period of time in the range between about 3 hours and about 96 hours.

3. A process according to claim 2 wherein the crystalline silica of the silicalite type is calcined in air for a period of time in the range between about 5 and about 72 hours.

4. A process according to claim 1 wherein the crystalline silica of the silicalite type is calcined in air at a temperature in the range between 500° C. and 800° C.

5. A process according to claim 4 wherein the crystalline silica of the silicalite type is calcined in air at a temperature in the range between 500° C. and 650° C.

6. A process according to claim 1 which comprises the step of calcining in air for at least 3 hours at a temperature of at least 500° C. a crystalline silica of the silicalite type having a silica to alumina atomic ratio of at least 120.

7. A process according to claim 6 wherein the crystalline silica of the silicalite type is calcined in air for a period of time in the range between 3 hours and 96 hours.

8. A process according to claim 7 wherein the crystalline silica of the silicalite type is calcined in air for a period of time in the range between 5 and 72 hours.

9. A process according to claim 6 wherein the crystalline silica of the silicalite type is calcined in air at a temperature comprised between 500° and 800° C.

10. A process according to claim 9 wherein the crystalline silica of the silicalite type is calcined in air at a temperature in the range between 550° and 650° C.

11. A process according to claim 6 which comprises the step of calcining in air for at least 3 hours at a temperature of at least 500° C. a crystalline silica of the silicalite type having a silica to alumina atomic ratio of at least 200.

12. A process according to claim 11 wherein the crystalline silica of the silicalite type is calcined in air for a period of time in the range between 3 hours and 96 hours.

13. A process according to claim 12 wherein the crystalline silica of the silicalite type is calcined in air for a period of time in the range between 5 and 72 hours.

14. A process according to claim 11 wherein the crystalline silica of the silicalite type is calcined in air at a temperature in the range between 500° and 800° C.

15. A process according to claim 14 wherein the crystalline silica of the silicalite type is calcined in air at a temperature in the range between 550° and 650° C.

* * * * *

UNITED STATES PATENT AND TRADEMARK OFFICE
CERTIFICATE OF CORRECTION

PATENT NO. : 4,772,456
DATED : September 20, 1988
INVENTOR(S) : DeClippeleir, Georges E.M.J. et al It is certified that error appears in the above—identified patent and that said Letters Patent is hereby corrected as shown below:

On the face of the patent:

[73], Assignee: "Labofina, S.A., Brussels, Belgium"

should read

"Cosden Technology, Inc., Dallas, Texas"

Signed and Sealed this

Twenty-first Day of March, 1989

*Attest:*

DONALD J. QUIGG

*Attesting Officer*    *Commissioner of Patents and Trademarks*